United States Patent
Furukawa

(10) Patent No.: US 6,338,823 B1
(45) Date of Patent: Jan. 15, 2002

(54) GAS CHROMATOGRAPH

(75) Inventor: Masanao Furukawa, Takaishi (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/292,315

(22) Filed: Apr. 15, 1999

(30) Foreign Application Priority Data

Jun. 30, 1998 (JP) .......................................... 10-183678

(51) Int. Cl.$^7$ .............................................. G01N 30/02
(52) U.S. Cl. ..................... 422/89; 73/23.35; 73/23.36; 73/23.39; 95/12; 95/19; 95/22; 95/23; 95/25
(58) Field of Search .............................. 422/89, 23.22; 73/23.35, 23.36, 23.39, 23.42; 95/12, 19, 22, 23, 25

(56) References Cited

U.S. PATENT DOCUMENTS

| | | | | |
|---|---|---|---|---|
| 5,163,979 A | * | 11/1992 | Patrick et al. | 55/21 |
| 5,391,221 A | * | 2/1995 | Fukushima et al. | 95/82 |
| 5,524,473 A | * | 6/1996 | Haskell | 73/1 G |
| 5,545,252 A | * | 8/1996 | Hinshaw et al. | 95/15 |

FOREIGN PATENT DOCUMENTS

| | | | |
|---|---|---|---|
| DE | 3642992 A | * | 6/1988 |
| JP | 402037716-a | * | 2/1990 |

* cited by examiner

Primary Examiner—Jill Warden
Assistant Examiner—Yelena Gakh
(74) Attorney, Agent, or Firm—Armstrong, Westerman, Hattori, McLeland & Naughton, LLP

(57) ABSTRACT

A gas chromatograph has a pressure sensor measuring a pressure in a sample introduction part, a flow control valve controlling carrier gas flow rate, a flow sensor measuring a flow rate of the carrier gas, a split flow path exhausting part of a carrier gas and sample from the introduction part, an exhaust valve placed in the sprit flow path, and a monitor screen. The controller controls the flow control valve to flow the carrier gas at the designated flow rate into the introduction part, reads an output of the pressure sensor after making the exhaust valve fully open, calculates a flow path resistance of the filter by using an output of the pressure sensor and a flow path resistance of the chromatographic column, and controls the monitor screen to display an indication for exchanging the filter when the calculated resistance reaches the preset value corresponding to a state in which the filter is stuffed.

20 Claims, 2 Drawing Sheets

GAS CHROMATOGRAPH

BACKGROUND OF THE INVENTION

This invention relates to a gas CHROMATOGRAPH for analyzing elements in a sample by introducing the sample into a chromatographic column through a sample introduction part and separating the elements through the column.

In an analysis of a sample by a gas chromatograph, the sample is injected into a sample introduction part with carrier gas also introduced therein. The sample joins with the carrier gas at the sample introduction part and is carried by the carrier gas into a chromatographic column. The sample is separated into its respective elements by interaction between a liquid, with which the inside surface of the column is lined, and the carrier gas. Differences among distribution coefficients of the elements cause this separation. Each of the elements exiting the column is introduced into a detection part connected to the outlet of the column, resulting in a chromatogram.

FIG. 1 is a schematic diagram of a typical gas chromatograph. A sample introduction part 1 evaporates a liquid sample injected therein. The sample introduction part 1 also introduces the carrier gas therein. The sample is delivered by the carrier gas into a chromatographic column 2 which is connected to the sample introduction part 1. A chromatographic column 2 separates the sample into its respective elements. A thermostatic chamber 3 controls temperature of the chromatographic column 2. A detection part 4 detects each element of the sample coming out of the chromatographic column 2. A carrier gas cylinder 5 supplies the carrier gas for the sample introduction part 1 through a carrier gas flow path 5a. A flow control valve 6 is placed in the carrier gas flow path 5a and controls a flow rate of the carrier gas. A split flow path 7 is connected to the sample introduction part 1 and exhausts part of the sample and the carrier gas. A filter 8 is placed in the split flow path 7 and prevents a needle valve 9 and split flow path 7 from becoming clogged. The needle valve 9 following the filter 8 is placed in the split flow path 7.

The sample introduced into the sample introduction part 1 is carried into the chromatographic column 2 by the carrier gas which is supplied by the carrier gas cylinder 5. The flow rate of the carrier gas is controlled by the flow control valve 6. The sample is separated in its respective elements through the chromatographic column 2. Each element of the sample coming out of the chromatographic column 2 is detected by the detection part 4.

Since only a small amount of sample can be introduced into the chromatographic column 2, almost all the sample and carrier gas are exhausted through the split flow path 7. The ratio of the amount of the sample exhausted through the split flow path 7 to the amount of the sample introduced into the chromatographic column 2 is called a split ratio. The split ratio is determined by the ratio of a flow path resistance of the chromatographic column 2 to that of the needle valve 9.

In the gas chromatograph, shown in FIG. 1, when the filter 8 is clogged, unnecessary pressure corresponding to a flow in the split flow path 7 is generated by the filter 8 even though the needle valve 9 may be left fully open. In such a case, it becomes difficult to set a pressure in the sample introduction part 1 properly low, and is therefore difficult to set the sample flow rate in the column 2 low. Therefore, each element in the sample does not separate suddenly from the other elements resulting in poor detection of the elements in the sample. To avoid such poor detection, an operator must often take the filter 8 off the split flow path 7 and observe whether the filter 8 is clogged to determine whether the filter 8 needs to be changed.

SUMMARY OF THE INVENTION

An object of the invention is to solve the above problems. Another object of this invention is to provide a gas chromatograph which can inform operators of a filter in a split flow path being clogged without taking the filter off the split flow path. Another object of this invention is to provide a gas chromatograph which can inform operators of the extent to which a filter is clogged without taking the filter off the split flow path. Another object of this invention is to provide a gas chromatograph which can instruct an operator to exchange a clogged filter without taking the filter off the split flow path.

A gas chromatograph analyzes elements in a sample by introducing the sample into a chromatographic column through a sample introduction part and separating the elements through the column, having a pressure measuring means for measuring a pressure in the introduction part, a flow control means, placed in a carrier gas flow path supplying a carrier gas into the introduction part, for controlling a flow rate of the carrier gas, a flow measuring means, placed in the carrier gas flow path, for measuring the flow rate of the carrier gas, a split flow path, connected to the sample introduction part, exhausting part of the carrier gas and the sample from the sample introduction part, a filter, placed in the split flow path, protecting the split flow path from being clogged, an exhaust valve, placed in the split flow path and following the filter, adjusting a flow rate in the split flow path, a monitor screen displaying information related to the filter, a controller calculating a flow path resistance of the filter based on a flow path resistance of the column, a pressure measured by the pressure measuring means in the exhaust valve opening, and a flow rate measured by the flow measuring means in the exhaust valve opening, the controller controlling the monitor screen to display information, by which necessity of exchange of the filter can be determined, based on the filter resistance.

The controller can obtain the column resistance "r" based on the following formula by using temperature of the column (t), inside diameter of the column (D), length of the column (L), pressure at the inlet of the column (P1), the pressure of the atmosphere (PA), viscosity (U) in the column, and a proportional coefficient (K1).

In the following sentence, pressure is described in the gauge pressure scale, and temperature is described in the Celsius temperature scale.

$$r = P1/F0$$

$$F0 = K1 \times (((D^2)/L) \times (D^2) \times (P1 + 2 \times PA) \times P1)/(U \times (273 + t))$$

The controller may also obtain the column resistance "r" from the following formula, where "f" is a slow rate measured by the flow measuring means when the exhaust valve is closed and P is a pressure measured by the pressure means when the exhaust valve is closed.

$$r = P/f$$

The controller may calculate the filter resistance from a following formula based on the column resistance "r", a pressure "P" measured by the pressure measuring means in the exhaust valve opening, and a flow rate "F" measured by the flow measuring means in the exhaust valve opening.

$$R = r \times P / (r \times F - P)$$

The controller compares the filter resistance to a preset resistance corresponding to a state in which the filter is clogged, and when the filter resistance becomes greater than the preset resistance, the controller indicates that the filter should be exchanged (e.g., on a monitor).

The pressure measuring means may be a pressure sensor sending an output thereof to the controller. The flow control means may be a flow control valve controlled by the controller. The flow measuring means may be a flow sensor sending an output thereof to the controller. The exhaust valve may be controlled by the controller. In this structure, the controller controls the exhaust valve to open, then reads outputs of the pressure sensor, and the flow sensor, and calculates the filter resistance.

The pressure measuring means may be a pressure gauge. The flow control means may be a flow valve. The flow measuring means may be a flowmeter. In such a case, pressures in the sample introduction part and a flow rate of the carrier gas are input into controller by an operator who reads them through the pressure gauge and flowmeter.

A buzzer 21 may be used instead of the monitor screen displaying information about necessity of exchange of the filter on the monitor screen. The controller makes the buzzer 21 sound when the controller finds necessity of exchange of the filter is determined based on the filter resistance.

A light 20 maybe used instead of the monitor screen displaying information about necessity of exchanging of the filter on the monitor screen. The controller makes the light 20 turn on when the controller determine it is necessary to exchange the filter based on the filter resistance.

The gas chromatograph mentioned above makes it possible to notify an operator of the extent to which the filter in a split flow path is stuffed without taking the filter off the split flow path. It is also possible to instruct an operator to exchange the filter in the split flow path. Therefore, this invention makes it possible to avoid carrying out the analysis with a clogged filter, that is, to avoid carrying out the analysis under a wrong split ratio.

DETAILED DESCRIPTION OF THE PREFERRED EMBODIMENT

Figure 1:
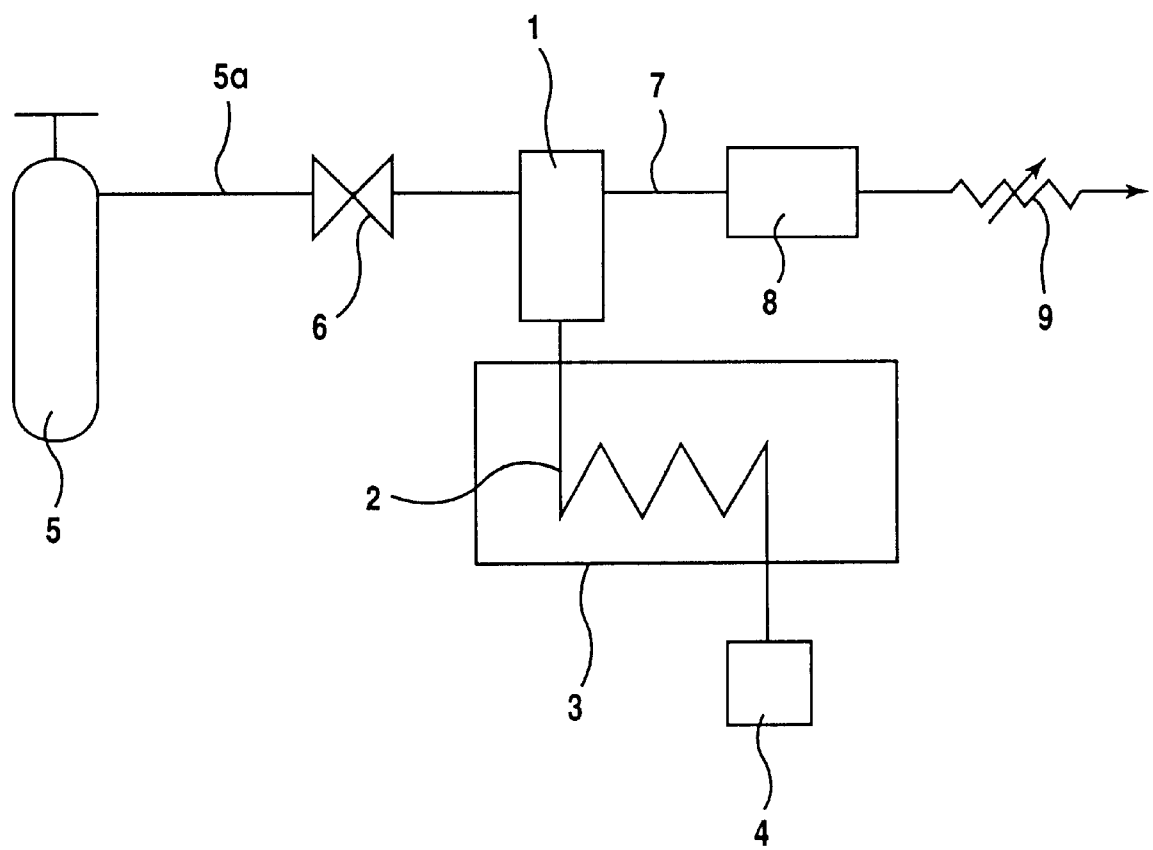
FIG. 1 is a schematic diagram showing a typical gas chromatograph.
Figure 2:
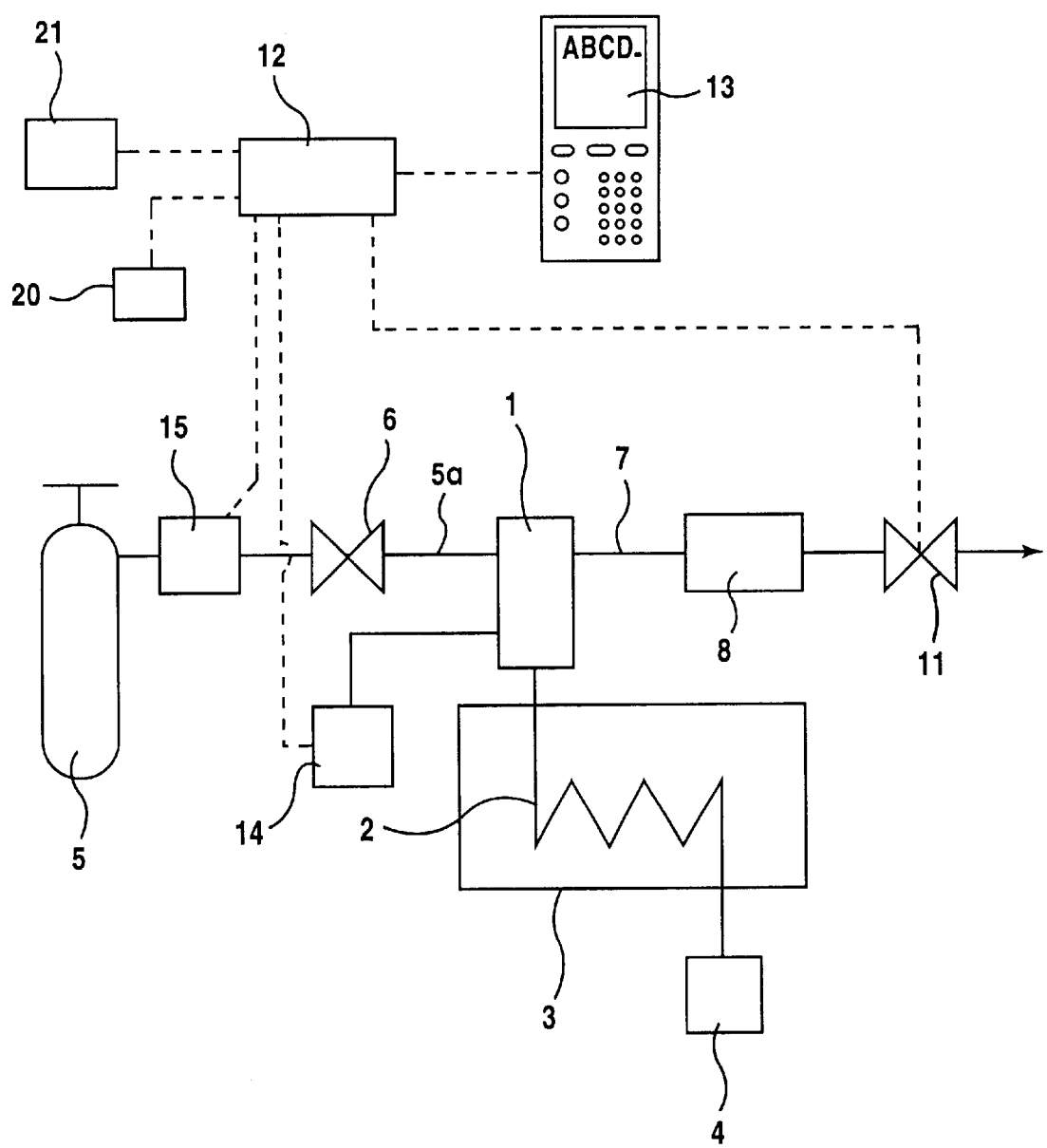
FIG. 2 is an schematic diagram showing a gas chromatograph of a preferred embodiment of this invention.

The following is a detailed description of a gas chromatograph of a preferred embodiment of the present invention, with reference to FIG. 2. In FIG. 2, the same symbols are used for the same or corresponding elements described above in the typical gas chromatograph shown in FIG. 1.

As shown in FIG. 2, a sample introduction part 1 evaporates a liquid sample injected therein. The sample introduction part 1 also introduces the carrier gas therein. The sample is delivered by the carrier gas into a chromatographic column 2 which is connected to the sample introduction part 1. A chromatographic column 2 separates the sample in its respective elements. A thermostatic chamber 3 controls temperature of the chromatographic column 2. A detection part 4 detects each element of the sample coming out of the chromatographic column 2. A carrier gas cylinder 5 supplies the carrier gas for the sample introduction part 1 through a carrier gas flow path 5a. The carrier gas flow path 5a connects between the carrier gas cylinder 5 and the sample introduction part 1. A flow control valve 6 is placed in the carrier gas flow path 5a and controls a flow rate of the carrier gas. A split flow path 7 is connected to the sample introduction part 1 and exhausts part of the sample and the carrier gas. A filter 8 is placed in the split flow path 7 and prevents an exhaust valve 11 and the split flow path 7 from being clogged. An exhaust valve 11 following the filter 8 is placed in the split flow path 7 and adjusts a flow rate in the split flow path 7. A monitor screen 13 displays information by which necessity of exchange of the filter 8 can be determined. For example, the information can be a flow path resistance of the filter 8, indication of exchanging the filter 8, and the like. A pressure sensor 14 measures a pressure in the sample introduction part 1 and outputs the measured pressure to the controller 12. The flow sensor 15, placed in the carrier gas flow path 5a, measures the flow rate of the carrier gas and outputs the measured flow rate to a controller 12. The controller 12 carries out a feedback control of the flow control valve 6 and the exhaust valve 11. The controller 12 also calculates a resistance of the filter 8 based on outputs of the pressure sensor 14 and the flow sensor 15 and displays the information about necessity of exchanging the filter 8 based on the calculated resistance.

To check the necessity of exchanging of the filter 8, an operator may instruct the controller 12 to check the filter 8 through a keyboard and the like, not shown in the Figures. Responding to the instruction, the control 12 controls the flow control valve 6 to flow the carrier gas into the sample introduction part 1 at the predetermined flow rate. At the same time, the controller 12 controls the exhaust valve 11 to be fully open. Since the exhaust valve 11 has little flow path resistance in this situation, we can obtain the following formula (Formula 1). In the following Formula 1, Formula 2, Formula 2a, Formula 3 and following specification, the following units are used for variables listed: P=kPa; F=ml/mn; R=kPa min/mil; r=kPa min/ml; FO=ml/min; t=° C.; D=mm; P1=kPa; PA=kPa; U=Pa-sec and f=ml/min. K1 does not have a dimension and the value of K1 is 9.9×10$^{-9}$ (according to the well-known Darcy's principal, the value of FO is 7677 in D=1, L=1, P1=100, PA=101.3, U=14.7×10$^{-7}$ and T=100.

$$P = r \times R \times F / (R + r) \qquad \text{(Formula 1)}$$

P: Pressure measured by the pressure sensor 14

F: Carrier gas flow rate

R: Flow path resistance of the filter 8 r: Flow path resistance of the chromatographic column 2

Therefore, we get the following formula (Formula 2) based on the above Formula 1 for calculation of the flow path resistance "R" of the filter 8.

$$R = r \times P / (r \times F - P) \qquad \text{(Formula 2)}$$

The flow rate F0 can be calculated empirically by the following procedures. According to the well-known Darcy's principle, Volume flow rate F(x) (x is a variable which shows a distance from the inlet of the column) in the column is determined under the following formula.

$$F(x) = -2K1 \times (D^4 / U) \times dP(x)/dx \qquad \text{formula A}$$

Since a mass flow rate is constant at any section of the column, the following formula is obtained.

$$F(x) = (PA / P(x)) \times F0 \qquad \text{formula B}$$

PA: pressure of the atmosphere

F0: Volume flow rate at the outlet of the column.

The following differential equation is obtained from the above formula A and B.

$$-2K1 \times (D^4/U) \times dP(x)/dx = (PA/P(x)) \times F0$$

Therefore, the following formula is obtained by integration of both the members.

$$-K(D^4/U) \times P^2(x) + C = PA \times F0 \times x \quad \text{formula C}$$

C: a constant.

When x equals 0, P(0) is P1+PA.

P1: gauge pressure at the inlet of the column Therefore, C is obtained from the above formula C.

$$-K(D^4/U) \times (P1+PA)^2 + C = 0$$

$$C = K(D^4/U) \times (P1+PA)^2 \quad \text{formula D}$$

On the other hand, when x equals L, P(L) is PA. (L:length of the column)

Therefore, the following formula is obtained from the above formula C.

$$-K(D^4/U) \times PA^2 + C = PA \times F0 \times L \quad \text{formula E}$$

Using the above formula D and formula E, we can obtain F0 by the following formula.

$$F0 = K \times D^4/(L \times U \times PA) \times P1(P1+2 \times PA) \quad \text{formula F}$$

Then F0 is compensated considering influence of temperature as follows.

$$F0 = K \times D^4/(L \times U \times PA) \times P1(P1+2 \times PA)/(273+t)$$

The flow path resistance "r" of the chromatographic column 2 is calculated by the controller 12 in advance based on the following formula (Formula 2a).

$$r = P1/F0 \quad \text{(Formula 2a)}$$

$$F0 = K1 \times (((D^2)/L) \times (D^2) \times (P1+2 \times PA) \times P1)/(U \times (273+t))$$

F0: flow rate in the column 2 t: temperature of the column 2

D: inside diameter of the column 2

L: length of the column 2

P1: pressure at the inlet of the column 2

PA: pressure of the atmosphere

U: viscosity of the carrier gas

K1: proportional coefficient

K1=D×Ts/(128×Ps×L)

Ts: temperature of a normal operating condition

Ps: pressure of a normal operating condition

We can choose, for example, the condition of Ts=298K and Ps=1 atm as the predetermined standard condition.

The controller 12 can get "P1" (pressure at the inlet of the column 2) by reading an output of the pressure sensor 14. The other values, which may be measured ahead of time, are input by a operator into the controller 12.

The controller 12 calculates the flow path resistance R of the filter 8 from the above Formula 2. After calculation of the resistance "R", the controller 12 compares the resistance "R" to a preset resistance which corresponds to a state in which the filter 8 is clogged enough to obstruct the analysis of the sample elements. When the resistance "R" is larger than the preset resistance, the controller 12 instructs the monitor screen 13 to display a message like "It is a time to exchange the filter".

Alternatively, or also, the monitor screen 13 may display only the resistance "R" calculated by the controller 12 as the message. The resistance "R" may also be displayed with the preset resistance.

Although in the above embodiment, several pre-measured values are input into the controller for calculation of the resistance of the column 2, the controller 12 can obtain the resistance of the column 2 without inputting such values. First the controller 12 controls the exhaust valve 11 to be closed, then controls the flow control valve 6 so that the pressure in the sample introduction part 1 is the predetermined pressure "P2". The controller 12 reads the flow rate "f" detected by the flow sensor 15, and calculates the flow path resistance "r" of the chromatographic column 2 by the following formula 3.

$$r = P2/F \quad \text{(formula 3).}$$

In the above embodiments, although the controller 12 controls a flow control valve 6 and exhaust valve 11 and reads outputs of the pressure sensor 14 and flow sensor 15, a flow control valve 6 and exhaust valve 11 may be manually controlled, and the pressure sensor 14 and flow sensor 15 may be a pressure gauge and flowmeter, respectively. In such a case, pressures in the sample introduction part 1 and a flow rate of the carrier gas are input into controller 12 by an operator who reads them through the pressure gauge and flowmeter.

In the above embodiments, a monitor screen is used to notify an operator of the necessity to exchange the filter in the split flow path. However, instead of using a monitor screen, a buzzer 21 or a light 20 may be used to notify an operator. In case of using the buzzer 21, the controller makes said buzzer 21 sound when the controller determines that exchange of said filter is necessary based on said filter resistance. In case of using the light 20, the controller makes the light 20 turn on when the controller determines that exchange of said filter is necessary based on said filter resistance.

According to the gas chromatograph mentioned above, it possible to notify an operator of the extent to which the filter in a split flow path is clogged without taking the filter off the split flow path. It is also possible to instruct an operator to exchange the filter in the split flow path. Therefore, this invention makes it possible to avoid carrying out the analysis with a clogged filter, that is, to avoid carrying out the analysis under a wrong split ratio.

A preferred embodiment was described above by way of example only. However, it should be understood that this invention covers all changes and modifications apparent to one skilled in the art without departing from essential characteristics thereof.

This application claims priority to Japanese Patent Application No. H10-183678 filed on Jun. 30, 1998, the disclosure of which is incorporated by reference in its entirely.

What is claimed is:

1. A gas chromatograph for analyzing elements in a sample by introducing said sample into and separating the elements through a column, comprising:

a chromatograph column with a sample introduction part;

pressure measuring means for measuring a pressure in said sample introduction part;

flow control means, placed in a flow path supplying carrier gas into said sample introduction part, for controlling a flow rate of said carrier gas;

flow measuring means, placed in said flow path, for measuring said flow rate of said carrier gas;

a split flow path, connected to said sample introduction part, exhausting part of said carrier gas and sample from said sample introduction part;

a filter, placed in said split flow path, protecting said split flow path from becoming clogged;

an exhaust valve, having an opening placed in said split flow path downstream of said filter, adjusting a flow rate in said split flow path;

a controller calculating a flow path resistance of said filter based on a flow path resistance of said column, a pressure measured by said pressure measuring means when said exhaust valve is in an opened position, and a flow rate measured by said flow measuring means when said exhaust valve open, said controller controlling a monitor screen to display information based on said filter resistance by which the necessity to exchange said filter can be determined; and the monitor screen connected to said controller displaying information related to said filter.

2. A gas chromatograph according to claim 1, wherein said controller obtains said column resistance "r" based on the following formula, using temperature of the column (t), inside diameter of the column (D), length of the column (L), pressure at the inlet of the column (P1), pressure of the atmosphere (PA), viscosity of said carrier gas (U), and a proportional coefficient (K1):

$$r = P1/F0$$

$$F0 = K1 \times (((D^2)/L) \times (D^2) \times (P1 + 2 \times PA) \times P1)/(U \times (273+t)).$$

3. A gas chromatograph according to claim 1, wherein said controller gets said column resistance "r" from the following formula based on a flow rate "f" measured by said flow measuring means when said exhaust valve is in a closed position and a pressure P measured by said pressure means when said exhaust valve is closed:

$$r = P/f.$$

4. A gas chromatograph according to claim 1, wherein said controller calculates said filter resistance from the following formula based on said column resistance "r", a pressure "P" measured by said pressure measuring means in said exhaust valve when open, and a flow rate "F" measured by said flow measuring means in said exhaust valve when open:

$$R = r \times P/(r \times F - P).$$

5. A gas chromatograph according to claim 1, wherein said controller compares said filter resistance to a clogged resistance corresponding to a state in which said filter is clogged and when said filter resistance becomes greater than said clogged resistance, said controller displays an indication to exchange said filter on said monitor screen.

6. A gas chromatograph according to claim 1, wherein said pressure measuring means is a pressure sensor sending an output thereof to said controller, said flow control means is a flow control valve controlled by said controller, said flow measuring means is a flow sensor sending an output thereof to said controller, said exhaust valve is controlled by said controller, and said controller controls said exhaust valve to open, then reads outputs of said pressure sensor, and said flow sensor, and calculates filter resistance.

7. A gas chromatograph according to claim 1, wherein said pressure measuring means is a pressure gauge, said flow control means is a flow valve, said flow measuring means is a flowmeter, and said exhaust valve is a needle valve.

8. A gas chromatograph for analyzing elements in a sample by introducing said sample into and separating the elements through a column, comprising:

a chromatograph column with a sample introduction part;

pressure measuring means for measuring a pressure in said introduction part;

flow control means, placed in a flow path supplying carrier gas into said introduction part, for controlling a flow rate of said carrier gas;

flow measuring means, placed in said flow path, for measuring said flow rate of said carrier gas;

a split flow path, connected to said sample introduction part, exhausting part of carrier gas and sample from said sample introduction part;

a filter, placed in said split flow path, protecting a said split flow path from being clogged;

an exhaust valve, having an opening placed in said split flow path downstream of said filter, adjusting a flow rate in said split flow path;

a controller calculating a flow path resistance of said filter based on a flow path resistance of said column, a pressure measured by said pressure measuring means when said exhaust valve is open, and a flow rate measured by said flow measuring means when said exhaust valve is open, said controller connected to a buzzer, which buzzer sounds when the controller determines that an exchange of said filter is necessary based on said filter resistance.

9. A gas chromatograph according to claim 8, wherein said controller obtains said column resistance "r" based on the following formula using temperature of the column (t), inside diameter of the column (D), length of the column (L), pressure at the inlet of the column (P1), pressure of the atmosphere (PA), viscosity of said carrier gas (U), and a proportional coefficient (K1):

$$r = P1/F0$$

where $$F0 = K1 \times (((D^2)/L) \times (D^2) \times (p1 + 2 \times PA) \times P1)/U \times (273+t)).$$

10. A gas chromatograph according to claim 8, wherein said controller obtains said column resistance "r" from the following formula based on a flow rate "f" measured by said flow measuring means in said exhaust valve when closed and a pressure "P" measured by said pressure means in said exhaust valve when closed:

$$r = P/f.$$

11. A gas chromatograph according to claim 8, wherein said controller calculates said filter resistance from the following formula based on said column resistance "r", a pressure "P" measured by said pressure measuring means when said exhaust valve is in the open position, and a flow rate "F" measured by said flow measuring means when said exhaust valve is open:

$$R = r \times P/(r \times F - P).$$

12. A gas chromatograph according to claim 8, wherein said controller compares said filter resistance to a clogged resistance corresponding to a state in which said filter is clogged and when said filter resistance becomes greater than said clogged resistance, said controller displays on said monitor screen an indication for exchanging said filter.

13. A gas chromatograph according to claim 8,
wherein said pressure measuring means is a pressure sensor sending an output thereof to said controller,
said flow control means is a flow control valve controlled by said controller,
said flow measuring means is a flow sensor sending an output thereof to said controller,
said exhaust valve is controlled by said controller,
said controller controls said exhaust valve to open, then reads outputs of said pressure sensor, and said flow sensor, and calculates said filter resistance.

14. A gas chromatograph according to claim 8,
wherein said pressure measuring means is a pressure gauge,
said flow control means is a flow valve,
said flow measuring means is a flowmeter.

15. A gas chromatograph for analyzing elements in a sample by introducing said sample into and separating the elements through a column, comprising:
a chromatograph column with a sample introduction part;
pressure measuring means for measuring a pressure in said sample introduction part;
flow control means, placed in a flow path supplying a carrier gas into said sample introduction part, for controlling a flow rate of said carrier gas;
flow measuring means, placed in said flow path, for measuring said flow rate of said carrier gas;
a split flow path, connected to said sample introduction part, exhausting part of said carrier gas and sample from said sample introduction part;
a filter, placed in said split flow path, protecting said split flow path from becoming clogged;
an exhaust valve having an opening, placed in said split flow path downstream of said filter, adjusting a flow rate in said split flow path;
a controller calculating a flow path resistance of said filter based on a flow path resistance of said column, a pressure measured by said pressure measuring means when said exhaust valve is in an open position, and a flow rate measured by said flow measuring means when said exhaust valve is in the open position, said controller connected to a light bulb which light bulb turns on when the controller determines an exchange of said filter is necessary based on said filter resistance.

16. A gas chromatograph according to claim 15, wherein said controller obtains said column resistance "r" based on the following formula, using temperature of the column (t), inside diameter of the column (D), length of the column (L), pressure at the inlet of the column (P1), pressure of the atmosphere (PA), viscosity of said carrier gas (U), and a proportional coefficient (K1):

$$r=P1/F0$$

where $$F0=K1\times(((D^2)/L)\times(D^2)\times(P1+2\times PA)\times P1)/U\times(273+t)).$$

17. A gas chromatograph according to claim 15, wherein said controller gets said column resistance "r" from the following formula based on a flow rate "f" measured by said flow measuring means when said exhaust valve is closed and a pressure P measured by said pressure means when said exhaust valve is closed:

$$r=P/f.$$

18. A gas chromatograph according to claim 15, wherein said controller calculates said filter resistance from the following formula based on said column resistance "r", a pressure "P" measured by said pressure measuring means when said exhaust valve is open, and a flow rate "F" measured by said flow measuring means when said exhaust valve is open:

$$R=r\times P/(r\times F-P).$$

19. A gas chromatograph according to claim 15, wherein said controller compares said filter resistance to a clogged resistance corresponding to a state in which said filter is clogged and when said filter resistance becomes greater than said clogged resistance, said controller displays an indication to exchange said filter on said monitor screen.

20. A gas chromatograph according to claim 15,
wherein said pressure measuring means is a pressure sensor sending an output thereof to said controller,
said flow control means is a flow control valve controlled by said controller,
said flow measuring means is a flow sensor sending an output thereof to said controller,
said exhaust valve is controlled by said controller, and
said controller controls said exhaust valve to open, then reads outputs of said pressure sensor, and said flow sensor, and calculates said filter resistance.

* * * * *